United States Patent
Nielsen et al.

(10) Patent No.: US 9,034,941 B2
(45) Date of Patent: *May 19, 2015

(54) HYDROPHILIC GELS FROM POLYURETHANE-BASED PHOTOINITIATORS

(75) Inventors: Christian B. Nielsen, Copenhagen NV (DK); Niels Joergen Madsen, Alleroed (DK); David George Anderson, York (GB); Petr Sehnal, York (GB)

(73) Assignee: Coloplast A/S, Humlebaek (DK)

( * ) Notice: Subject to any disclaimer, the term of this patent is extended or adjusted under 35 U.S.C. 154(b) by 142 days.

This patent is subject to a terminal disclaimer.

(21) Appl. No.: 13/805,134

(22) PCT Filed: Jun. 22, 2011

(86) PCT No.: PCT/DK2011/050229
§ 371 (c)(1),
(2), (4) Date: Dec. 18, 2012

(87) PCT Pub. No.: WO2011/160641
PCT Pub. Date: Dec. 29, 2011

(65) Prior Publication Data
US 2013/0089582 A1    Apr. 11, 2013

(30) Foreign Application Priority Data

Jun. 22, 2010 (DK) ................. 2010 70282
Jul. 27, 2010 (DK) ................. 2010 70342
Dec. 22, 2010 (DK) ................. 2010 70572
Jun. 9, 2011 (DK) ................. 2011 70288

(51) Int. Cl.
*C08G 18/67* (2006.01)
*C08G 65/18* (2006.01)
(Continued)

(52) U.S. Cl.
CPC ............. *C08L 75/12* (2013.01); *A61L 27/34* (2013.01); *A61L 27/52* (2013.01); *A61L 29/085* (2013.01);
(Continued)

(58) Field of Classification Search
CPC ..... A61L 27/34; A61L 29/085; A61L 29/145; A61L 27/52; C08L 5/12; C08G 18/329; C08G 18/5024; C08G 18/6688; C08G 18/758; C08G 2210/00; C08J 3/075; C08J 2375/12
USPC .................................. 424/400; 522/168, 174
See application file for complete search history.

(56) References Cited

U.S. PATENT DOCUMENTS 4,477,326 A    10/1984 Lin
6,031,044 A    2/2000 Kokel et al.
(Continued)

FOREIGN PATENT DOCUMENTS

CN    1817914    8/2006
CN    101495162    7/2009
(Continued)

OTHER PUBLICATIONS

Oliphant et al. "Melt grafting of a basic monomer on to polyethylene in a twin-screw extruder: reaction kinetics." Polymer, v. 36, n. 8, 1995, pp. 1597-1603.
(Continued)

*Primary Examiner* — Blessing M Fubara
(74) *Attorney, Agent, or Firm* — Coloplast Corp., Coloplast A/S; Nick Baumann

(57) ABSTRACT

The present invention relates to the use of polymeric photoinitiators based on polyalkyletherurethane backbones in the production of hydrophilic gels, in particular hydrogels. The invention relates to methods for manufacturing hydrophilic gels using said polymeric photoinitiators, and the hydrophilic gels thus obtained.

10 Claims, 10 Drawing Sheets

Figure 1:
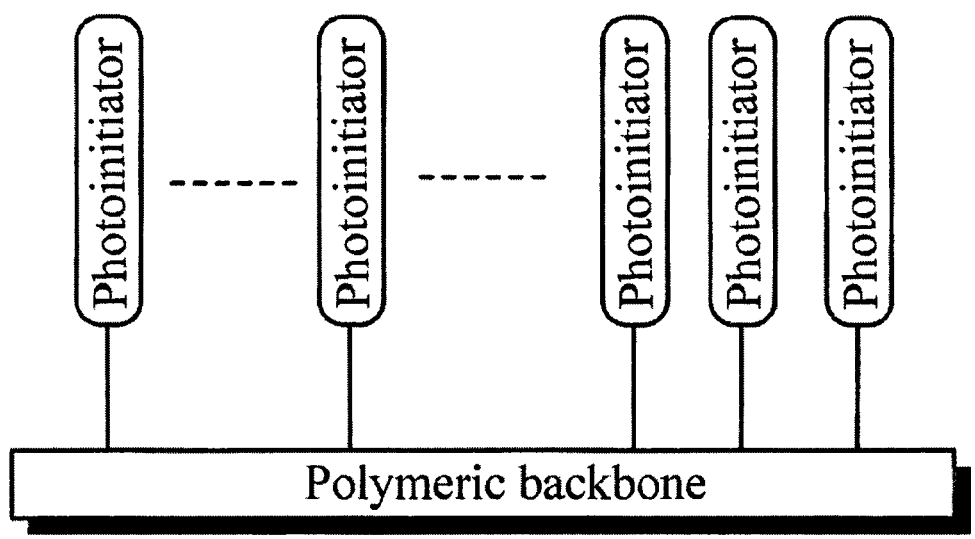
Figure 2:
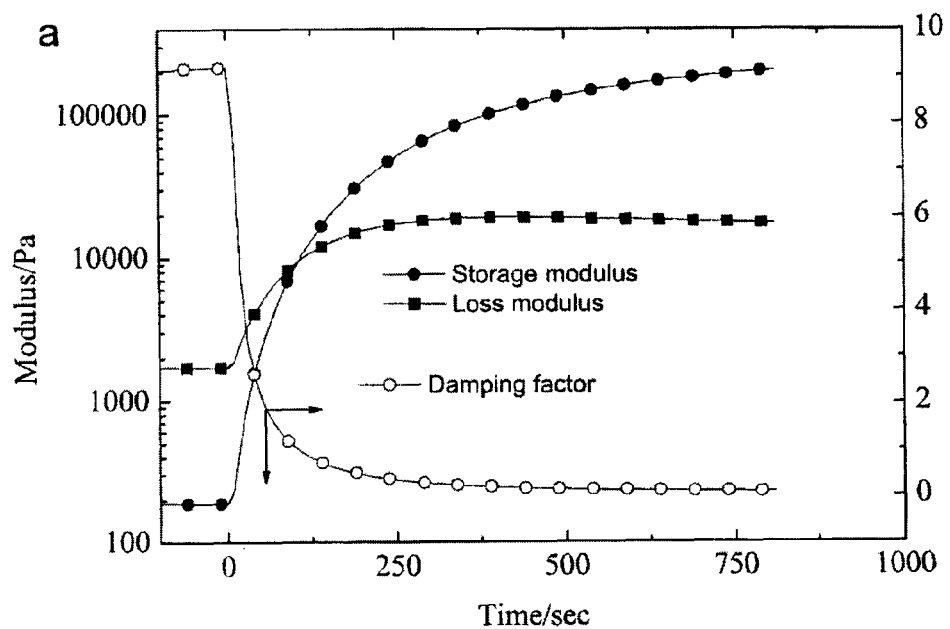
Figure 3:
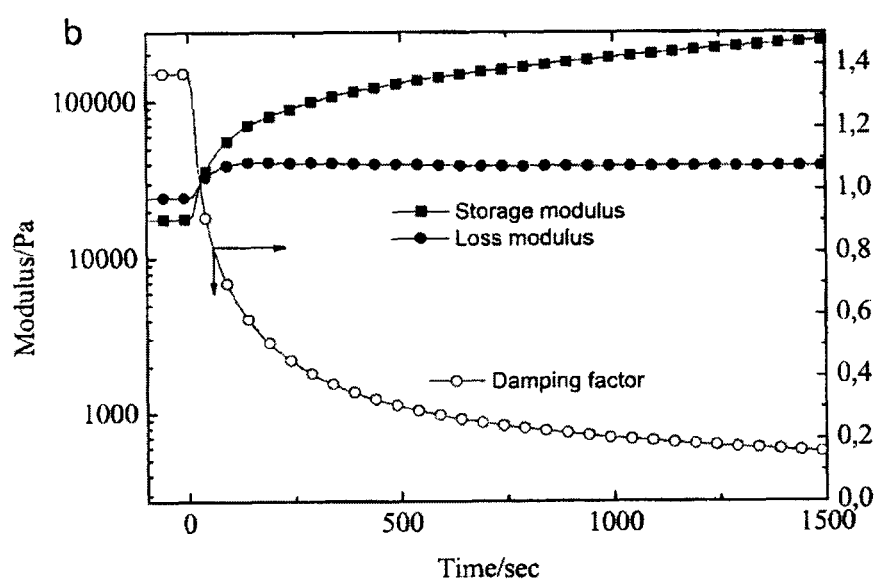
Figure 4:
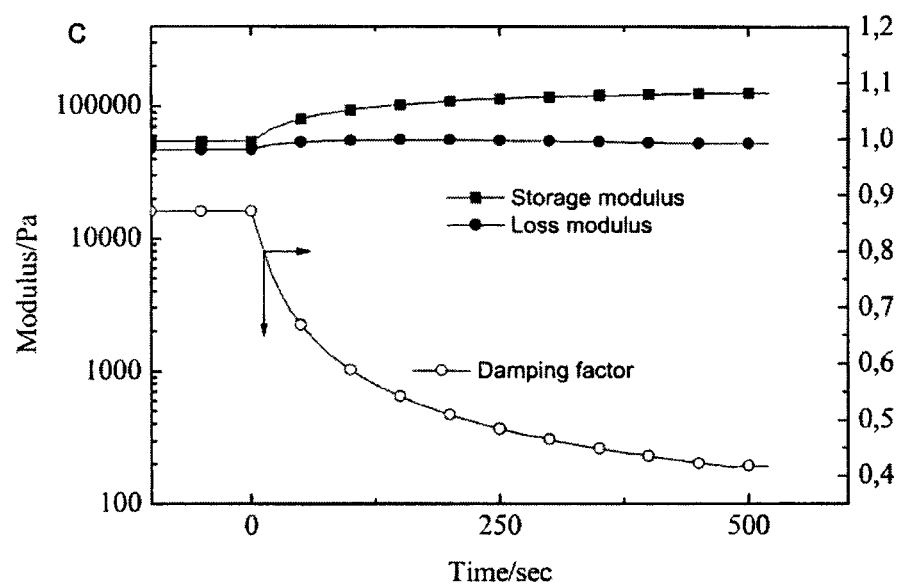
Figure 5:
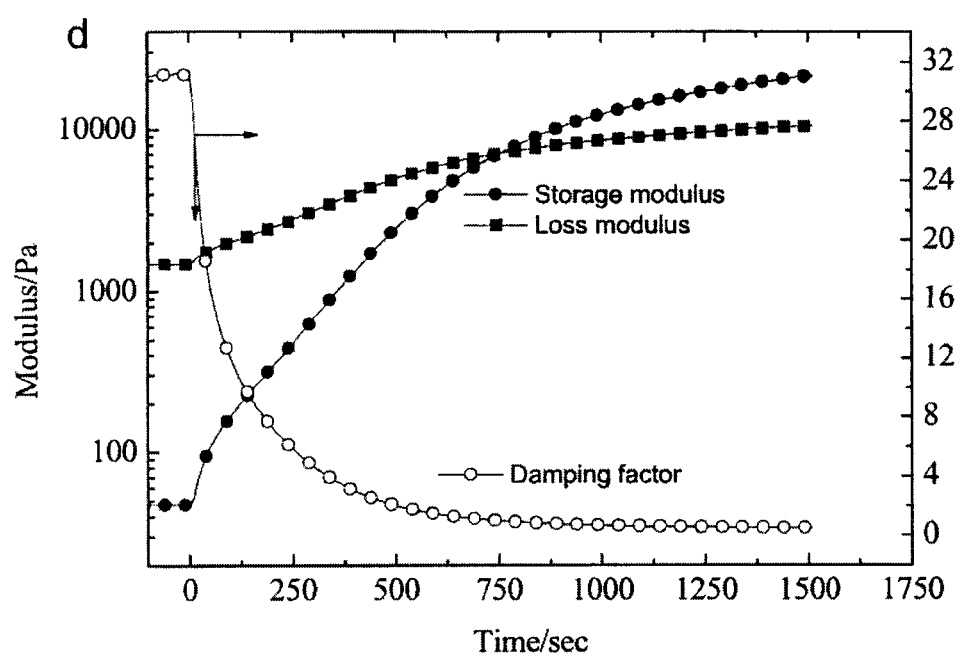
Figure 6:
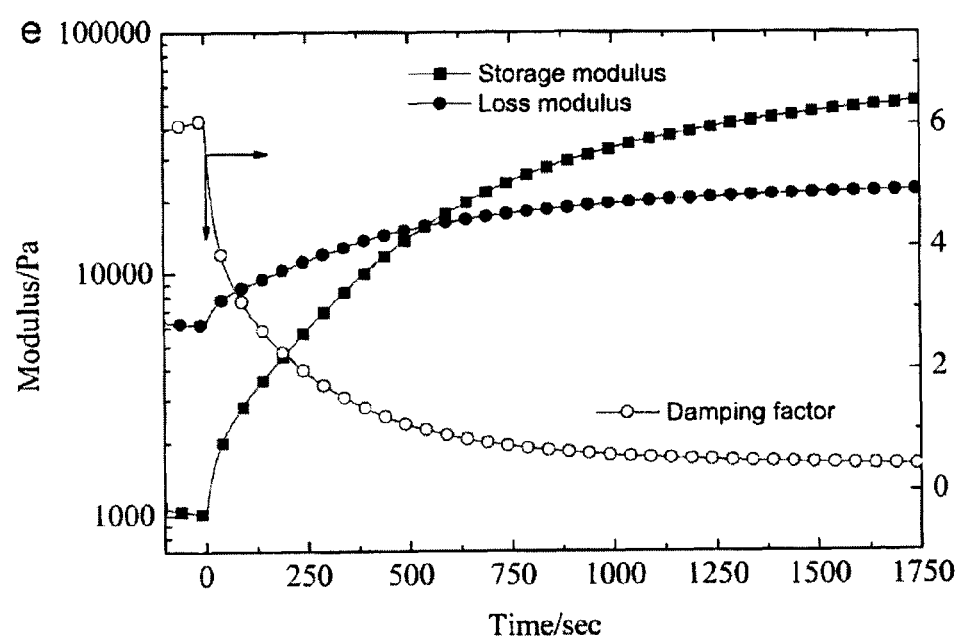
Figure 7:
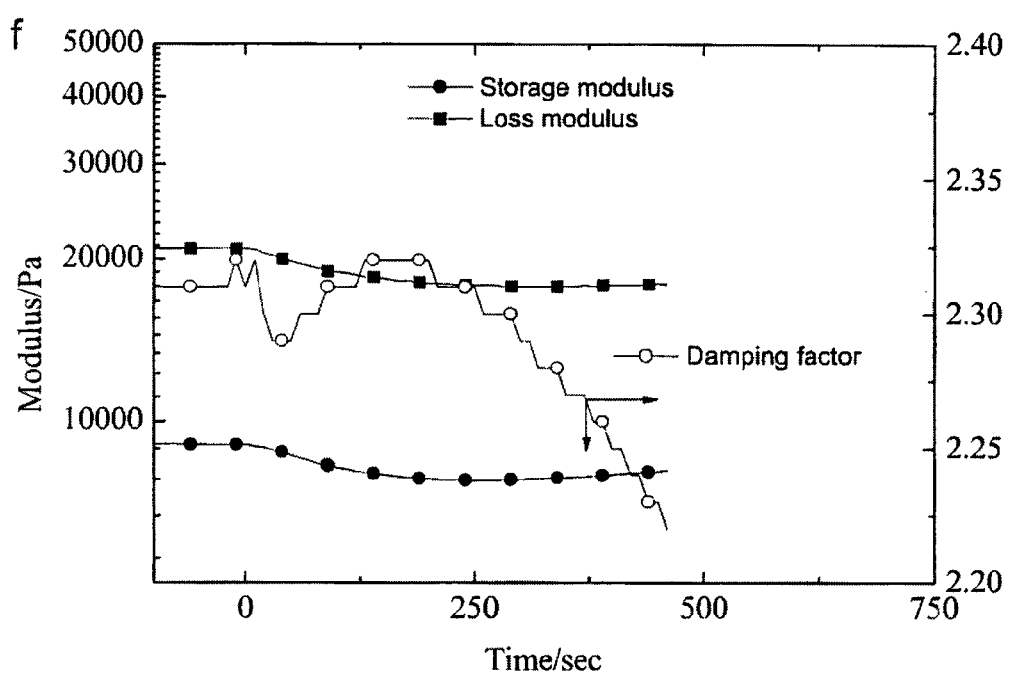
Figure 8:
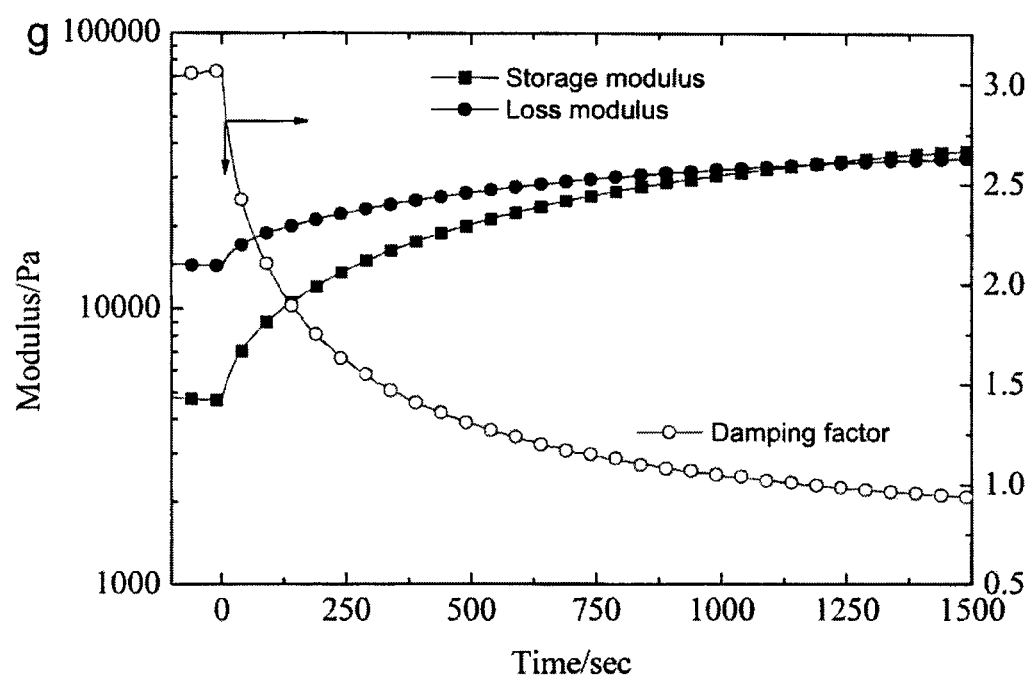
Figure 9:
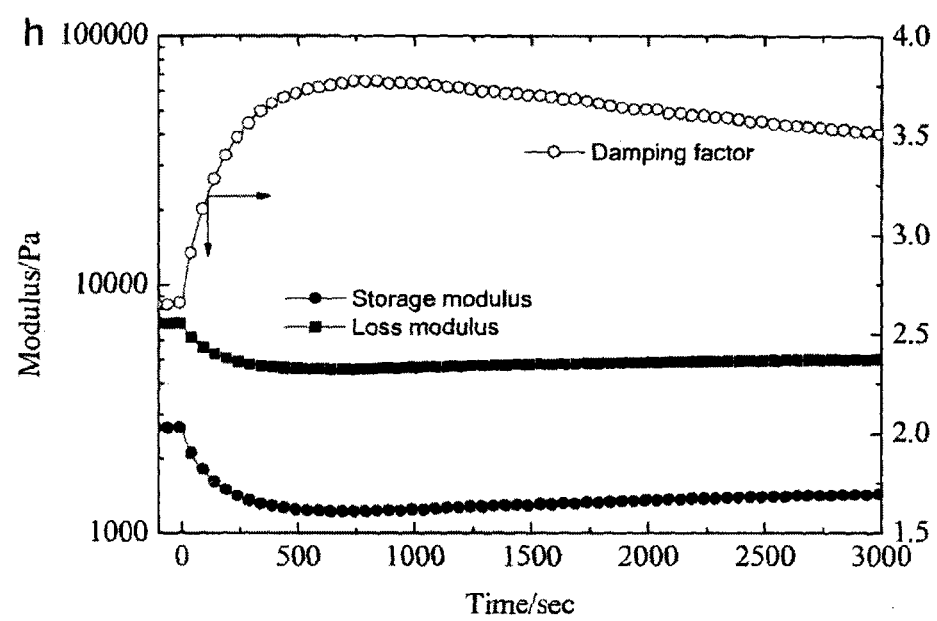

(51) Int. Cl.
- *A61K 9/00* (2006.01)
- *C08L 75/12* (2006.01)
- *A61L 27/34* (2006.01)
- *A61L 27/52* (2006.01)
- *A61L 29/08* (2006.01)
- *A61L 29/14* (2006.01)
- *A61L 31/10* (2006.01)
- *A61L 31/14* (2006.01)
- *C08F 2/50* (2006.01)
- *C08G 18/32* (2006.01)
- *C08G 18/50* (2006.01)
- *C08G 18/66* (2006.01)
- *C08G 18/75* (2006.01)
- *C08G 73/02* (2006.01)
- *C08J 3/075* (2006.01)
- *C08J 3/24* (2006.01)

(52) U.S. Cl.
CPC .............. *A61L 29/145* (2013.01); *A61L 31/10* (2013.01); *A61L 31/145* (2013.01); *C08F 2/50* (2013.01); *C08G 18/329* (2013.01); *C08G 18/5024* (2013.01); *C08G 18/6688* (2013.01); *C08G 18/758* (2013.01); *C08G 73/028* (2013.01); *C08G 2210/00* (2013.01); *C08J 3/075* (2013.01); *C08J 3/24* (2013.01); *C08J 2375/12* (2013.01)

(56) References Cited

U.S. PATENT DOCUMENTS

| | | |
|---|---|---|
| 2009/0098359 A1 | 4/2009 | Waller, Jr. et al. |
| 2010/0049146 A1* | 2/2010 | Nielsen et al. ............... 604/265 |

FOREIGN PATENT DOCUMENTS

| | | |
|---|---|---|
| EP | 0 441 524 | 8/1991 |
| EP | 0 849 300 | 6/1998 |
| EP | 2060589 | 5/2009 |
| WO | WO 91/05809 | 5/1991 |
| WO | WO 2008/012325 | 1/2008 |
| WO | WO 2008012325 A2 * | 1/2008 |

OTHER PUBLICATIONS

Krivoguz et al. "Structures and Properties of Polypropylene/Low-Density Polyethylene Blends Grafted with Itaconic Acid in the Course of Reactive Extrusion." Journal of Applied Polymer Science, v. 102, 2006, pp. 1746-1754.

Sun et al. "Melt free-radical grafting of glycidyl methacrylate onto polypropylene." Angew. Makrom, Chem, vol. 229, n. 3982, pp. 1-13, 1995.

Bhuyan et al. "N,N-diethyl Dithiocarbamato Group Induced Photografting of Methyl Methacrylate onto Polyurethane." Journal of Applied Polymer Science, v.112, 64-71 (2009).

Dotcheva et al. "Ultraviolet-Induced Crosslinking of Solid Poly(ethylene oxide)." Journal of Applied Polymer Science, v. 64, n. 12, Jun. 20, 1997, pp. 2299-2307.

Wei et al. "Novel PU-type polymeric photoinitiator comprising side-chain benzophenone and coinitiator amine for photopolymerization of PU acrylate." Polymers for Advanced Technologies, v. 19, 2008; pp. 1763-1770.

Flory, Principles of Polymer Chemistry; Cornell University Press: Ithaca, NY, 1953; Chapter IX.

Almdal, "Towards a Phenomenological Definition of the term 'Gel'", Polymer Gels and Networks, 1 (1993), pp. 5-17.

Gilbert et al. "Essentials of Molecuar Photochemistry", Angew. Chem. 103 (1991) Nr. 11, p. 1554-1555.

Gould et al. "Novel Self-Initiating UV-Curable Resins: Generation Three," Proceedings from RadTech Europe 05, vol. 1, Oct. 18-20, 2005, p. 245-251.

Nguyen et al. "Malemide Reactive Oligomers" Proceedings from RadTech Europe 03, vol. 1, Nov. 3-5, 2003, pp. 589-594.

Fouassier "Excited-State Reactivity in Radical Polymerisation Photoinitiators" in Radiation Curing in Polymer Science and Technology. Ch. 1, pp. 1-61, 1993.

Kopeinig et al. "Further Covalently Bonded Photoinitiators" Proceedings from RadTech Europe 05, vol. 2, Oct. 18-20, 2005, pp. 375-381.

Wei et al. "Novel Photosensitive Thio-Containing Polyurethane as Macrophotoinitiator Comprising Side-Chain Benzophenone and Co-Initiator Amine for Photopolymerization," Macromolecules, 40 (2007), pp. 2344-2351.

"Finer features for functional microdevices," Nature, v. 412, Aug. 16, 2001, pp. 697-698.

Mezger. "The Rheology Handbook," Vincentz Network, Hannover, 2006, pp. 7-18.

* cited by examiner

HYDROPHILIC GELS FROM POLYURETHANE-BASED PHOTOINITIATORS

This is a national stage of PCT/DK11/050229 filed Jun. 22 2011 and published in English, which has a priority of Denmark no. PA 2010 70282 filed Jun. 22, 2010, Denmark no. PA 2010 70342 filed Jul. 27, 2010, Denmark no. PA 2010 70572 filed Dec. 22, 2010, and Denmark no. PA 2011 70288 filed Jun. 9, 2011, hereby incorporated by reference.

FIELD OF THE INVENTION

The present invention relates to polymeric photoinitiators based on polyalkyletherurethane backbones and their use in the production of gels. The invention relates to methods for manufacturing hydrophilic gels using said polymeric photoinitiators, and the gels thus obtained.

BACKGROUND OF THE INVENTION

Curing of coatings through ultraviolet (UV) radiation, thereby resulting in a coating for use as a gel (e.g. a hydrogel), requires efficient methods of initiating the chemical reaction responsible for the curing process. Cross-linking of polymeric material through generation of radical species upon irradiation with UV light is widely used to produce hydrogels for medical device coatings. Coating compositions with polyvinylpyrrolidone and a photoinitiator as the main constituents, which are cured with UV irradiation, are often used for producing hydrogels. The photoinitiators used in these processes can be either oligomeric or polymeric. Oligomeric photoinitiators are partially free to diffuse to the surface of the cured material, thereby rendering these substances exposed to the environment.

Polymeric photoinitiators are disclosed in EP 0 849 300, WO 2008/012325 and Wei et al. Polymers for Advanced Technologies, 2008, vol. 18, no. 12, p. 1763-1770.

OBJECT OF THE INVENTION

The object of the present invention is to provide a method for the manufacture of gels, as well as the gels which result from these methods.

SUMMARY OF THE INVENTION

It has been found by the present inventors that certain polymeric photoinitiators can be used in the formation of gels.

In a broad aspect, therefore, the present invention relates to a method for the manufacture of a gel, said method comprising the steps of a. providing a matrix composition comprising a polymeric photoinitiator of the general formula I:

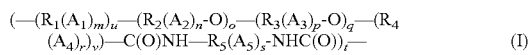
(I)

wherein $R_2$, $R_3$ and $R_5$ can each independently be selected from C1-C25 linear alkyl, C3-C25 branched alkyl, C3-C25 cycloalkyl, aryl and heteroaryl groups such as any aromatic hydrocarbon with up to 20 carbon atoms;

$R_1$ and $R_4$ are each independently selected from C1-C25 linear alkyl, C3-C25 branched alkyl, C3-C25 cycloalkyl, aryl, heteroaryl, hydrogen, —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, hydrazine, azines, hydrazides, polyethylenes, polypropylenes, polyesters, polyamides, polyacrylates, polystyrenes, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group;

m, n, p, r and s are real numbers, from 0 to 10, provided that the sum of n+p+s is a real number greater than 0;
o and q are real numbers from 0 to 10000;
u and v are real numbers from 0 to 1;
t is an integer from 1 to 10000; and
$A_1$, $A_2$, $A_3$, $A_4$ and $A_5$ are identical or different photoinitiator moieties, b. curing the matrix composition obtained in step a. by exposing it to UV radiation, and
c. exposing the matrix composition to a swelling medium, thus providing a gel, wherein step c. may take place before or after step b.

The invention also provides a gel, particularly a hydrophilic gel, obtainable via the method of the invention, and a medical device comprising the gel of the invention.

In the case where the swelling medium is water, a hydrogel is obtained.

LEGENDS TO THE FIGURE

FIG. 1 illustrates a general motif of polymeric photoinitiators, with photoinitiator moieties pendant on a polymeric backbone.

FIGS. 2-9 display the change in mechanical properties when a sample of pristine photoinitiator is exposed to UV light at 120° C. for various polyurethanes of the Examples. At time t=0 irradiation with UV light is started and an instant increase in both the loss and storage modules takes place. When the moduli are equal, a transition from liquid to solid proceeds by further UV radiation. If the sample is exposed to water after this curing step, a hydrogel material is obtained.

Figure 10:
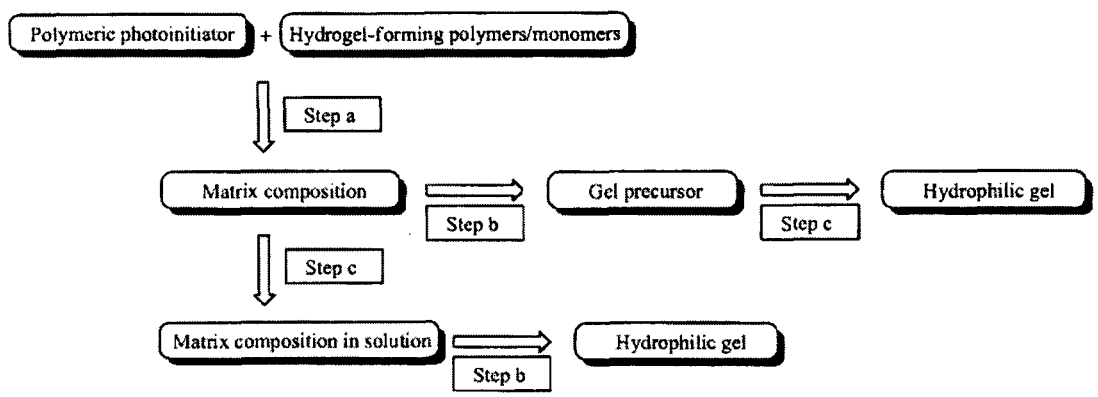

FIG. 10 illustrates the processes of the invention.

DETAILED DISCLOSURE OF THE INVENTION

Definitions

"Optionally-substituted" means optionally-substituted with one or more substituents selected from the group consisting of C1-C25 linear, branched or cyclic alkyl, aryl, —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates. Preferably, the one or more substituents are selected from the group consisting of —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates. Most preferably, the substituent is selected from the group consisting of —OH, —CN, halogens, amines, amides, alcohols, ethers, thioethers, sulfones and derivatives thereof, sulfonic acid and derivatives thereof, and sulfoxides and derivatives thereof.

Hydrophilic

A material is described as hydrophilic if it has a natural affinity to water. Hydrophilic materials are defined as those which have a contact angle with water of less than 90°, preferably less than 80°, more preferably less than 75° and most preferably less than 50° (see ASTM D7334-08) measured with an advancing contact angle measurement. In short, the method for measuring the advancing contact angle of a water drop on a surface, is done by deposition of the water droplet (~5-20 μL) controlled in size within 0.1 μL using a hypodermic syringe. A goniometer is then adjusted such that the interior angle of each of the two points of contact of the drop can be determined. Two angle measurements (one on each drop edge) of three drops on the specimen is determined and the contact angle for the specimen is the average of these six angle measurements.

A hydrophilic polymer is likely to contain atoms with high electronegative values such as oxygen and nitrogen. Materials which are hydrophilic according to the above definition will also have an affinity for short-chain (e.g. C1-C8) alcohols and glycerol. Specific examples of hydrophilic polymers are polyethylene oxides, polyvinylacetates, polyvinylpyrolidones, amine functional polymers e.g. poly(2-ethyl-2-oxazoline), acrylics, polyethers, polyalkylethersulfonate, polyvinyl alcohols.

Hydrophilic Gels

A gel is an interconnected, rigid network with pores of submicrometer dimensions and polymeric chains whose average length is greater than a micrometer. The term "gel" is discussed in detail in Flory, P. J. Principles of Polymer Chemistry; Cornell University Press: Ithaca, N.Y., 1953; Chapter IX.

A definition of a gel is provided in Polymer Gels and Networks, 1 (1993), 5-17: A gel is a soft, solid or solid-like material of two or more components one of which is a liquid, present in substantial quantity. Solid-like gels are characterized by the absence of an equilibrium modulus, by a storage modulus, $G'(\omega)$, which exhibits a pronounced plateau extending to times at least of the order of seconds, and by a loss modulus, $G''(\omega)$, which is considerably smaller than the storage modulus in the plateau region.

In the interest of characterizing the efficiency of a photoinitiator in cross-linking polymeric matrices, the transition from a liquid to a solid material is of importance. Liquids are characterized by having $G''(\omega) > G'(\omega)$ and correspondingly, solids are characterized by $G''(\omega) < G'(\omega)$. The transition from liquid to solid, often referred to as the gel-point, is defined as when $G''(\omega) = G'(\omega)$. The cure time defined as the time from initiation of a curing process to when $G''(\omega) = G'(\omega)$ or $\tan \delta = 1$ is a characteristic measure of the efficiency of a photoinitiator in a specific matrix composition.

Specific Embodiments of the Invention

The present invention provides hydrophilic gels, hydrophilic gel precursors and methods for their manufacture.

The invention provides a method for the manufacture of a gel, said method comprising the steps of
a. providing a matrix composition comprising a polymeric photoinitiator of the general formula I:

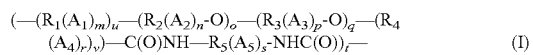

$$(-(R_1(A_1)_m)_u-(R_2(A_2)_n-O)_o-(R_3(A_3)_p-O)_q-(R_4(A_4)_r)_v)-C(O)NH-R_5(A_5)_s-NHC(O)_t- \quad (I)$$

b. curing the matrix composition obtained in step a. by exposing it to UV radiation, and
c. exposing the matrix composition to a swelling medium, thus providing a gel,
wherein step c. may take place before or after step b.

As the photoinitiators are bound within the matrix composition after curing, the likelihood of photoinitiators of low molecular weight leaching from the surface of the cured material is reduced.

$R_2$, $R_3$ and $R_5$ can each independently be selected from C1-C25 linear alkyl, C3-C25 branched alkyl, C3-C25 cycloalkyl, aryl and heteroaryl groups such as any aromatic hydrocarbon with up to 20 carbon atoms. Suitably, $R_2$ and $R_3$ are each independently selected from C1-C25 linear alkyl, C3-C25 branched alkyl and C3-C25 cycloalkyl, preferably C1-C25 linear alkyl. $R_5$ may be selected from the group consisting of C3-C25 cycloalkyl and aryl groups.

$R_1$ and $R_4$ are each independently selected from C1-C25 linear alkyl, C3-C25 branched alkyl, C3-C25 cycloalkyl, aryl, heteroaryl, hydrogen, —OH, —CN, halogens, amines (e.g. —NR'R", where R' and R" are alkyl groups, suitably C1-C25 alkyl groups), amides (e.g. —CONR'R" or R'CONR"—, where R' and R" are alkyl groups, suitably C1-C25 alkyl groups), alcohols, ethers, thioethers, sulfones and derivatives thereof, sulfonic acid and derivatives thereof, sulfoxides and derivatives thereof, carbonates, isocyanates, nitrates, acrylates, hydrazine, azines, hydrazides, polyethylenes, polypropylenes, polyesters, polyamides, polyacrylates, polystyrenes, and polyurethanes. $R_1$ and $R_4$ may each independently be selected from C1-C25 linear alkyl, C3-C25 branched alkyl and C3-C25 cycloalkyl.

$R_1$ and $R_4$ may be end-functionalized with alcohol, ether, urethane or amine groups, alternatively other nucleophilic groups, in either one or both ends. Alternatively, $R_1$ and $R_4$ can be considered as originating from chain extenders, where suitable extenders can include ethylene diamine, diethylene triamine, triethylene tetramine, propylene diamine, butylenes diamine, hexamethylene diamine, cyclohexylene diamine, piperazine, 2-methyl-piperazine, phenylene diamine, tolylene diamine, xylylene diamine, tris(2-aminoethyl) amine, 3,3'-dinitrobenzidine, 4,4'-methylenebis(2-chloroaniline), 3,3'-dichloro-4,4'-bi-phenyl diamine, 2,6-diaminopyridine, 4,4'-diaminodiphenylmethane, menthane diamine, m-xylene diamine and isophorone diamine.

$R_1$ and $R_4$ may also be selected from the group consisting of hydrazine, azines such as acetone azine, substituted hydrazines such as dimethyl hydrazine, 1,6-hexamethylene-bishydrazine, and carbodihydrazine, hydrazides of dicarboxylic acids and sulfonic acids such as adipic acid mono- or dihydrazide, oxalic acid dihydrazide, isophthalic acid, dihydrazide, tartaric acid dihydrazide, 1,3-phenylene disulfonic acid dihydrazide, omega-amino-caproic acid dihydrazide, hydrazides made by reacting lactones with hydrazine such as gamma-hydroxylbutyric hydrazide, bis-semi-carbazide, bis-hydrazide carbonic esters of glycols such as any of the glycols mentioned above.

When $R_1$ and $R_4$ are alkyl and aryl groups, they may be substituted with one or more substituents selected from CN; OH; azides; esters; ethers; amides (e.g. —CONR'R" or R'CONR"—, where R' and R" are alkyl groups, suitably C1-C25 alkyl groups); halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group.

In order to obtain a hydrophilic polymer suitable for hydrogel formation, $R_2$ and $R_3$ should preferably be ethylene segments. $R_1$, $R_3$, and $R_5$ can optionally be hydrophobic in nature provided that the resulting polymer overall can be considered hydrophilic. Preferably, $R_1$, $R_3$ and $R_5$ are hydrophilic e.g. polyethylene oxides. Co-polymers where $R_2$ is an ethylene segment and $R_3$ is a propylene segment also fall within the present invention, again, with the limitation that the stoichiometric ratios do not provide a resulting polymer which is hydrophobic. Furthermore, $R_2$ and $R_3$ can be longer-chain alkyl segments, but, if so, $R_1$, $R_3$ and $R_5$ should be hydrophilic in nature to make the entire polymer hydrophilic.

In the polymeric photoinitiators of Formula (I), m, n, p, r and s are real numbers, from 0 to 10, provided that the sum of n+p+s is a real number greater than 0 (i.e. at least one of $A_2$, $A_3$ and $A_5$ are present). In other words, the polymeric photoinitiators of Formula (I) are those in which at least the isocyanate group ($R_5$) or the polyether groups ($R_2$, $R_3$) comprise photoinitiators.

In the polymeric photoinitiators of Formula (I), o and q are real numbers from 0 to 10000. Suitably, o and q are real numbers from 0-5000, preferably 100-2000.

In the polymeric photoinitiators of Formula (I), u and v are independently real numbers from 0 to 1. Preferably u and v are independently real numbers greater than zero.

In the polymeric photoinitiators of Formula (I), t is an integer from 1 to 10000. Suitably, t is an integer from 1 to 5000, preferably 100-2000.

As a minimum, the sum n+p+s is greater than zero. Hence, s may be greater than or equal to 1. Alternatively or additionally, p may be greater than or equal to 1. n may also be greater than or equal to 1. Alternatively or additionally, r and v are greater than or equal to 1. r may be zero, as may m. p and q may be greater than or equal to 1.

It may be possible that the sum m+n+p+r+s is 1.

The indices o, m, n, o, p, q, r, s, v and u in the general formula (I) represent an average/sum and the formula (I) thereby represents alternating, periodic, statistical/random, block and grafted copolymers. An example of a random copolymer may be the copolymer ABAAABABAABABAA having the formula $(A_2B_1)_5$ by applying a nomenclature similar to formula I.

An example of the identity of formula I applied to a photoinitiator described in the present invention is given in Scheme 1.

spectrum and the photoinitiator absorption spectrum. Another desired property is a minor or no overlap between the photoinitiator absorption spectrum and the intrinsic combined absorption spectrum of the other components in the matrix composition.

Suitably, the photoinitiator moieties are pendant on the polymer. This means that they are attached to the polymer at points other than at the polymer ends.

The photoinitiator moieties of the invention may independently be cleavable (Norrish Type I) or non-cleavable (Norrish Type II). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. The photoinitiator moieties of the invention are efficient in transforming light from the UV or visible light source to reactive radicals which can abstract hydrogen atoms and other labile atoms from polymers and hence effect covalent cross-linking. Optionally, amines, thiols and other electron donors can be either covalently linked to the polymeric photoinitiator or added separately or both. The addition of electron donors is not required but may enhance the overall efficiency of cleavable photoinitiators according to a mechanism similar to that described for the non-cleavable photoinitiators below.

Suitably, the photoinitiator moieties of the invention are all non-cleavable (Norrish Type II). For reference, see e.g. A. Gilbert, J. Baggott: "Essentials of Molecular Photochemistry", Blackwell, London, 1991). Non-cleavable photoinitiator moieties do not break down upon excitation, thus providing fewer possibilities for the leaching of small molecules from the matrix composition. Excited non-cleavable photoinitiators do not break down to radicals upon excitation, but abstract a hydrogen atom from an organic molecule or, more Scheme 1: Examples of applying formula I to a photoinitiator. Formula I then reads $(CH_2CH(CH_2OPhCOPh)_1O)_o(CH_2CH_2O)_1$—$C(O)NHC_6H_{10}CH_2C_5H_{10}NHC(O))_t$.
The value of o × t then determines the molecular weight of the photoinitiator.

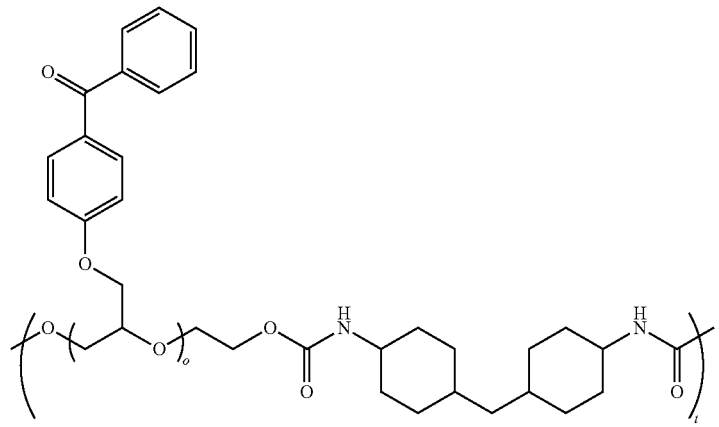

Photoinitiator and Photoinitiator Moieties

In the polymeric photoinitiators of Formula (I), $A_1$, $A_2$, $A_3$, $A_4$ and $A_5$ are identical or different photoinitiator moieties.

In the present invention, a photoinitiator is defined as a moiety which, on absorption of light, generates reactive species (ions or radicals) and initiates one or several chemical reactions or transformation. One preferred property of the photoinitiator is good overlap between the UV light source efficiently, abstract an electron from an electron donor (such as an amine or a thiol). The electron transfer produces a radical anion on the photoinitiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones and related ketones such as thioxanthones, xanthones, anthraquinones, fluorenones, dibenzosuberones, benzils, and phenyl ketocoumarins are important examples of non-cleavable photoinitiators. Most amines with a CH bond in α-position to the nitrogen atom and many thiols will work as electron donors. The photoinitiator moieties of the invention are preferably non-cleavable.

Self-initiating photoinitiator moieties are within the scope of the present invention. Upon UV or visible light excitation, such photoinitiators predominantly cleave by a Norrish type I mechanism and cross-link further without any conventional photoinitiator present, allowing thick layers to be cured. Recently, a new class of P-keto ester based photoinitiators has been introduced by M. L Gould, S. Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz. After base-catalyzed Michael addition of the ester to polyfunctional acrylates, a network is formed with a number of quaternary carbon atoms, each with two neighbouring carbonyl groups.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photoinitiators and at the same time spontaneously polymerize by radical addition across the maleimide double bond. In addition, the strong UV absorption of the maleimide disappears in the polymer, i.e. maleimide is a photobleaching photoinitiator; this could make it possible to cure thick layers.

So, in an embodiment of the invention, the photoinitiator moieties include at least two different types of photoinitiator moieties. Preferably, the absorbance peaks of the different photoinitiators are at different wavelengths, so the total amount of light absorbed by the system increases. The different photoinitiators may be all cleavable, all non-cleavable, or a mixture of cleavable and non-cleavable. A blend of several photoinitiator moieties may exhibit synergistic properties, as is e.g. described by J. P. Fouassier: "Excited-State Reactivity in Radical Polymerization Photoinitiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethylbenzophenone], [thioxanthone+methylthiophenyl morpholinoalkyl ketone].

Furthermore, it has recently been found that covalently linked 2-hydroxy-1-(4-(2-hydroxyethoxy)phenyl)-2-methylpropan-1-one, which is commercially available with the trade name Irgacure 2959, and benzophenone in the molecule 4-(4-benzoylphenoxyethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20, 2005, vol. 2, p. 375-81, Vincentz. This shows that different photoinitiator moieties may show significant synergistic effects when they are present in the same oligomer or polymer.

Each and every one of the above-discussed types of photoinitiators and photoinitiator moieties may be utilised as photoinitiator moieties in the polymeric photoinitiators of the present invention.

In an embodiment of the polyalkyletherurethane derived photoinitiator according to the invention, $A_1$, $A_2$, $A_3$, $A_4$ and $A_5$, identical or different photoinitiator moieties, are selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, silane, maleimides, and derivatives thereof. The group can also consist of derivatives of the photoinitiator moieties listed.

Suitably, $A_1$, $A_2$, $A_3$, $A_4$ and $A_5$ are selected from the group consisting of benzoin ethers, phenyl hydroxyalkyl ketones, phenyl aminoalkyl ketones, benzophenones, thioxanthones, xanthones and derivatives thereof. The group can also consist of derivatives of the photoinitiator moieties listed.

Typically, at least one of $A_1$, $A_2$, $A_3$, $A_4$ and $A_5$ is an optionally-substituted benzophenone moiety. In this regard, the benzophenones may be "optionally substituted" with one or more moieties defined as per $R^1$, above.

Polymeric Photoinitiators of the Invention

Polyurethane-Derived Photoinitiators

The polyurethane-derived photoinitiators can be synthesized by reacting a polyalkyloxide-based photoinitiator with a diisocyanate optionally using a catalyst such as a tin salt, an organic tin ester, for example, dibutyltin dilaurate or a tertiary amine such as triethyl diamine, N,N,N',N'-tetramethyl-1,3-butane diamine or other recognized catalysts for urethane reactions known in the art. Further examples are stannous octoate, triethylamine, (dimethylaminoethyl) ether, morpholine compounds such as β,β'-dimorpholinodiethyl ether, bismuth carboxylates, zinc bismuth carboxylates (e.g. BICAT catalysts from Shephard chemicals), iron(III) chloride, potassium octoate, potassium acetate, and DABCO (diazabicyclo[2.2.2]octane), and also a mixture of 2-ethylhexanoic acid and stannous octoate. The mentioned catalysts may also be used in combination with each other and typically in the amounts of 5 to 200 parts per million of the total weight of prepolymer reactants. An exemplified method for synthesizing polyurethane-based photoinitiators is depicted in Scheme 2.

Scheme 2: An exemplified method for preparing a polyurethane-based photoinitiator.

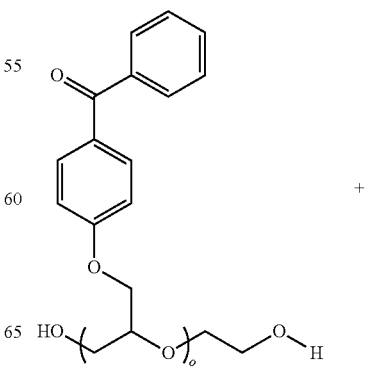

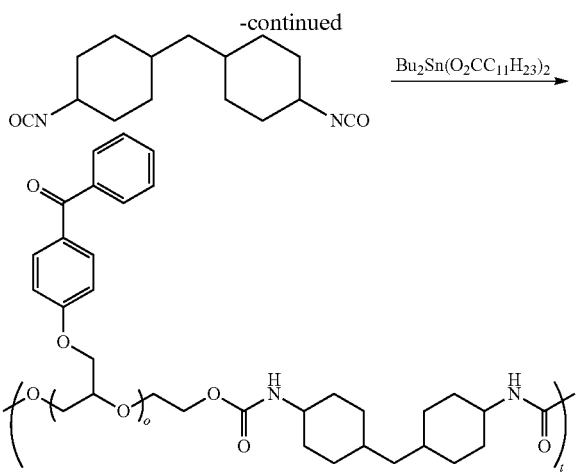

The isocyanate depicted in Scheme 2 is bis(4-isocyanato-cyclohexyl)methane (trade name HMDI). Various other isocyanates may be used including α,ω-alkylene diisocyanates having from 5 to 20 carbon atoms such as tetramethylene diisocyanate, hexamethylene diisocyanate, trimethylhexamethylene diisocyanate, isophorone diisocyanate, diethylbenzene diisocyanate, decamethylene 1,10-diisocyanate, cyclohexylene 1,2-diisocyanate and cyclohexylene 1,4-diisocyanate, 1,12-dodecane diisocyanate, 2-methyl-1,5-pentamethylene and the aromatic isocyanates such as 2,4- and 2,6-tolylene diisocyanate, 4,4-diphenylmethane diisocyanate, 1,5-naphthalene diisocyanate, dianisidine diisocyanate, tolidine diisocyanate and bis(4-isocyanatocyclohexyl)methane. Polymeric types of polyisocyanate are also of interest, such as neopentyl tetra isocyanate, m-xylylene diisocyanate, tetrahydronaphthalene-1,5 diisocyanate, and bis(4-isocyanatophenyl)methane.

The end-groups present on the polyurethane-based photoinitiator are dependent on the stoichiometry of the reactants. If for example, the end-groups of the polymer are supposed to be free hydroxy groups, an excess of the polyalkylether reactant should be used in comparison with the amount of the isocyanate. On the other hand, if free isocyanate groups should be present as end-groups an excess of the isocyanate should be used.

It can also be envisioned that more than one polyalkylether photoinitiator moiety is used.

Other polyurethane-based photoinitiators are reported in the literature, such as the benzophenone derivatized polyurethanes in J. Wei, H. Wang, X. Jiang, J. Yin, *Macromolecules*, 40 (2007), 2344-2351): An example of such photoinitiators is presented in Scheme 3.

Scheme 3: Synthesis of polymeric polyurethane-based photoinitiators as described in J. Wei, H. Wang, X. Jiang, J. Yin, *Macromolecules*, 40 (2007), 2344-2351).

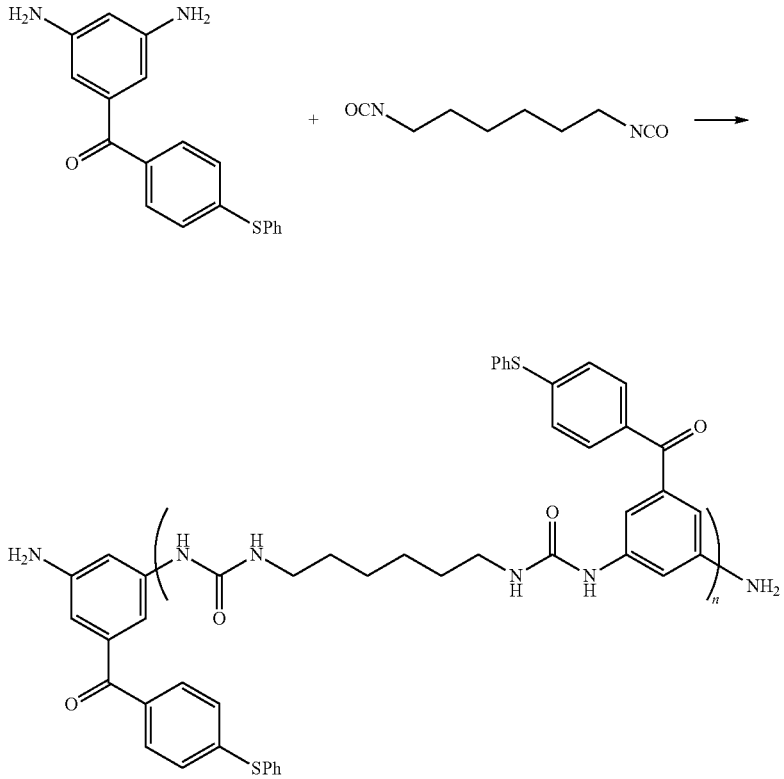

Despite various reports of similar photoinitiators as the one depicted in Scheme 3, there have been no reports of polyurethane-based photoinitiators with polyalkylether segments in between the urethane functionalities.

One particular attractive property of coating compositions consisting solely of polyurethane-derived photoinitiators is the additional physical cross-linking induced by the urethane segments as compared to for example a polymeric photoinitiator with no possibility for hydrogen bonding. This additional physical cross-linking should render the polyalkyletherurethane-based photoinitiators more efficient in producing—for example—hydrogels, in comparison to a polyalkylether-based photoinitiator.

An example of a polyurethane-based photoinitiator possessing the properties described above is depicted in Scheme 4.

are preferred, such as triethyl amine, dimethyl ethanolamine, N-morpholine, and the like, and mixtures thereof. It is recognized that primary or secondary amines may be used in place of tertiary amines, if they are sufficiently hindered to avoid interfering with the chain extension process. The pre-polymer can then be processed to form the polyurethane photoinitiators described in the present invention by:

(1) Dispersion of the prepolymer by shear forces with emulsifiers (external emulsifiers, such as surfactants or internal emulsifiers, having anionic and/or cationic groups as part of or pendant to the polyurethane backbone, and/or as end groups on the polyurethane backbone).

Scheme 4: Synthesis of a polymeric photoinitiator, with a diol derivative of benzophenone, diisocyanate and a polyethylene glycol as the starting materials.

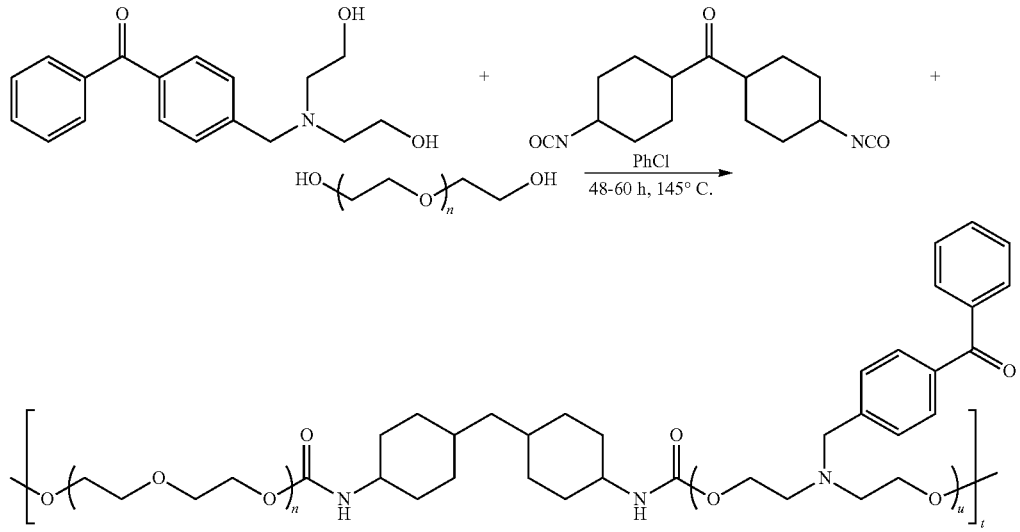

Utilizing the sum-formula,

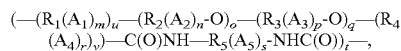

the polymer shown in Scheme 4 can be written as,

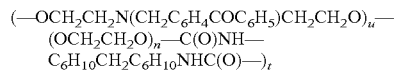

This example represents a general method of incorporating photoinitiators substituted with diethanolamine into a polyurethane.

Several other methods exist for the synthesis of the polyurethane-based photoinitiators, with some of the important methods outlined below:

Initially, an isocyanate-terminated prepolymer is formed by reacting a photoinitiator polyalkylether with an isocyanate and possibly one or more chain extender(s). Such prepolymers are characterized by having isocyanate groups and/or alcohol, amine or other nucleophilic functionalities as end-groups in the polymer. Furthermore, the prepolymer has a lower molecular weight than the targeted polyurethane photoinitiator. The prepolymers can be formed without the use of a catalyst, however, a catalyst chosen from the catalysts described above, can be preferred in some instances. In instances, where the prepolymer has pendent carboxyl groups, an optional neutralization of the prepolymer will result in carboxylate anions, thus having an increased solubility or dispersibility in water. Suitable neutralizing agents include tertiary amines, metal hydroxides, ammonium hydroxide, phosphines, and other agents well known to those skilled in the art. Tertiary amines and ammonium hydroxide (2) Acetone process, where a prepolymer is formed with or without the presence of acetone, methylethylketone, and/or other polar solvents that are non-reactive and easily distilled. If necessary the prepolymer is further diluted in the above-mentioned solvents and chain extended with chain extenders mentioned previously. Water is added to the chain-extended polyurethane and the solvents are distilled off. A variation of this process would be to chain-extend the prepolymer after its dispersion into water.

(3) Melt dispersion process, where an isocyanate-terminated prepolymer is formed, and then reacted with an excess of ammonia or urea to form a low molecular weight oligomer having terminal urea or biuret groups. This oligomer is dispersed in water and chain-extended by methylolation of the biuret groups with formaldehyde.

(4) Ketazine and ketimine processes, hydrazines or diamines are reacted with ketones to form ketazines or ketimines. These are added to a prepolymer and remain inert to the isocyanate. As the prepolymer is dispersed in water, the hydrazine or diamine is liberated, and chain extension takes place as the dispersion is taking place.

(5) Continuous process polymerization, where an isocyanate-terminated prepolymer is formed. This prepolymer is pumped through high shear mixing head(s) and dispersed into water and then chain-extended at said mixing head(s), or dispersed and chain extended simultaneously at the mixing head(s). This is accomplished by multiple streams consisting of prepolymer (or neutralized prepolymer), optional neutralizing agent, water, and optional chain extender and/or surfactant.

(6) Reverse feed process, where water and optional neutralizing agent(s) and/or extender amine(s) are charged to the prepolymer under agitation. The prepolymer can be neutralized before water and/or diamine chain extenders are added.

(7) Solution polymerisation.

(8) Bulk polymerisation, including but not limited to extrusion processes.

In the present invention, $M_w$ (the weight averaged molecular weight) is used to characterize the polymeric photoinitiators. Efficiency of the polymeric photoinitiator is related to how well the photoinitiator is blended with the gel-forming polymer(s) or monomer(s). Amongst important parameters in this respect is the molecular weight of the photoinitiator. A molecular weight which is too high does not allow for good miscibility of the polymeric photoinitiator with other components of the matrix composition. In particular, if the chemical nature and molecular weight of the polymeric photoinitiator and the gel-forming polymer(s) are markedly different, a poor miscibility is obtained, which in turn results in a matrix composition that is difficult to cure.

In one embodiment, therefore, the photoinitiator according to the invention suitably has a weight averaged molecular weight between 0.2 kDa and 100 kDa, more preferably between 0.2 kDa and 75 kDa, preferably between 0.5 and 50 kDa. Suitably, the weight averaged molecular weight of the photoinitiator is 0.50-45 kDa and the loading of benzophenone moiety is greater than 0% and below 50%. As seen from the examples, the molecular weight of the used photoinitiators are between 29 kDa and 78 kDa.

Matrix Composition

In one embodiment, the polymeric photoinitiators of formula (I) are combined with one or more gel-forming polymers and/or gel-forming monomers to form a matrix composition. Gel-forming polymers are polymers which—due to their hydrophilic nature—retain a swelling medium such as water within the polymer structure, allowing a gel to be formed, once the matrix composition is cured and swollen.

In particular, the gel-forming polymer may be a hydrogel-forming polymer. A hydrogel-forming polymer is selected from the group comprising polyacrylates, polyalkylethers such as polyethylene oxide, polyurethanes, polyamides, polyethylene vinyl acetates, polyvinylpyrrolidone and co-polymers and blends thereof. Preferably, the hydrogel-forming polymer is selected from the group consisting of poly-alkylethers, polyurethanes, polyethylene vinyl acetate.

A gel-forming monomer is a monomer which produces a gel-forming polymer when polymerised. A hydrogel-forming monomer is one which produces hydrogel-forming polymers as set out above. Suitable hydrogel-forming monomers may be selected from the group consisting of acrylate monomers, N-vinylpyrrolidone, and epoxide monomers and, for example, monomers with two or more hydroxyl and/or amino functionalities, such as diethanol and aminoethanol.

For providing a hydrophilic gel after a curing step, a polymerization of the monomeric entities occurs in conjunction with cross-linking. After the curing step, the cross-linked composition is then swelled with a swelling medium such as water, C1-C5 alcohols, glycerol and polyethylene glycol (PEG), preferably PEG-2000.

Other possible components in the matrix composition include anti-oxidants such as BHT (2,6-bis(1,1-dimethylethyl)-4-methylphenol), Irganox 1010 (from Ciba) and similar structures. Therapeutic additives are also possible components in the matrix composition. When such additional components are present in the matrix composition, they may be added directly at the same time as the matrix composition is formed, at any point prior to curing, or as a component of the swelling medium. The latter is most preferred.

Curing

The matrix composition of the invention is cured by exposing it to UV radiation.

Curing can either occur in the molten state, or in a solution. The latter comprises steps, where the matrix composition is dissolved in a suitable solvent and for example spray-coated on to a tube, and subsequently exposed to UV radiation. The solvent can afterwards either be evaporated or remain in the coating and function as a swelling medium to provide the desired gel.

The ultraviolet spectrum is divided into A, B and C segments where UV A extends from 400 nm to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelengths. In particular, scattering phenomena are less pronounced at longer wavelength, thus giving a larger penetration depth in the material. Thus, photoinitiators which absorb, and can induce curing at longer wavelength, are of interest. By judicially choosing substituents on the aromatic moieties, the absorption spectrum of the polymeric photoinitiator can to some extent be red-shifted, which would then facilitate curing at comparatively greater depths.

Multi-photon absorption can also be used to cure samples using light sources emitting at wavelengths twice or even multiple times the wavelength of light needed for curing in a one-photon process. For example, a composition containing a photoinitiator with an absorption maximum at 250 nm could possibly be cured with a light source emitting at 500 nm utilizing a two-photon absorption process, provided that the two-absorption cross section is sufficiently high. A multi-photon initiated cure process could also facilitate greater spatial resolution with respect to the cured area (exemplified in Nature 412 (2001), 697 where a 3D structure is formed by a two-photon curing process).

In the present invention, curing is primarily initiated by exposing the matrix composition to high energy irradiation, preferably UV light. The photoinitiated process takes place by methods described above and which are known per se, through irradiation with light or UV irradiation in the wavelength range from 250 to 500 nm. Irradiation sources which may be used are sunlight or artificial lamps or lasers. Mercury high-pressure, medium pressure or low-pressure lamps and xenon and tungsten lamps, for example, are advantageous. Similarly, excimer, solid state and diode based lasers are advantageous. Even pulsed laser systems can be considered applicable for the present invention. Diode based light sources in general are advantageous for initiating the chemical reactions.

In the curing process the polymeric photoinitiator transforms the matrix composition in a chemical process induced by light.

Auto-Curing

The polymeric photoinitiators described here can both facilitate curing of a surrounding matrix but since the photoinitiators themselves are polymers they can also "auto-cure", meaning that the polymeric photoinitiators can solely constitute the matrix composition that is cured with UV irradiation. This is particularly relevant when at least one of $A_1, A_2, A_3, A_4$ and $A_5$ is an optionally-substituted benzophenone moiety.

In one aspect, therefore, the invention provides a method for manufacturing a hydrophilic gel as provided herein, in which the matrix composition consists of a polymeric photoinitiator of the general formula I.

The "auto-curing" method suitably takes place with steps a., b. and c. occurring in alphabetical order, directly after one another (i.e. with no intermediate steps). In one aspect of this "auto-curing" method, the method consists of steps a., b. and c. alone.

A one-component system—as provided by the "auto-curing" method—provides advantages, in that the polymeric photoinitiators are thermoplastic. As such, they become less viscous under higher shear rate, making them easier to process in an extrusion process. In contrast, for example, polyvinyl pyrrolidone cannot be extruded. All details and structural refinements of the polymeric photoinitiator provided herein are aimed at providing photoinitiators suitable for use in the "auto-curing" method.

In addition, the polymeric photoinitiators of the "auto-curing" method may comprise the sole component of the matrix composition; i.e. the matrix composition may consist of the polymeric photoinitiators. This provides the advantage that additives (e.g. plasticizers, viscosity modifiers) can be avoided, thereby reducing the chances of low molecular weight components from leaching from the cross-linked matrix composition.

Gel-State

To provide the gel of the invention, the matrix composition is exposed to a swelling medium such as water, C1-C5 alcohols, glycerol and polyethylene glycol (PEG), preferably PEG-2000. The compositions are thus swelled to provide a gel. Contact with the swelling medium may take place before or after curing of the matrix composition. The swelling medium may be in its pristine state, or present in combination with other substances, e.g. in a saline solution or a body fluid. Species present in the gaseous state in equilibrium with a significant portion present in their liquid form also constitute a swelling medium.

The matrix composition may be cured by exposure to UV before or after exposure to the swelling medium. If cured first, a "dry", cured matrix composition (=gel precursor) is obtained. If exposed to swelling medium first, a hydrophilic gel can be provided in a one-step process, as the curing step takes place in the presence of the swelling medium. In other words, the swelling medium for the hydrophilic gel is the solvent for the curing step. In terms of method steps, step c. may take place before or after step b. Suitably, step c takes place before step b.

In particular, the method may consist of steps a. b. and c. (i.e. the only steps in the method are a. b. and c.).

A gel is characterized as a swellable material, however, insoluble in the swelling medium. By hydrogel is meant a material comprised mainly of a water soluble or water swellable material. The gel material is characterized in terms of its rheological properties and in its dry state. In particular, the storage and the loss modulus are used to characterize the mechanical properties of the materials (T. G. Mezger: "The Rheology Handbook", Vincentz Network, Hannover, 2006). As described above, curing of a matrix composition is followed by monitoring the change of G'(ω) and G"(ω) as a function of UV exposure time. In the examples used to describe the present invention, a frequency of 1 Hz is used to probe the rheological properties and further the samples were heated to 120° C. during testing.

The invention also relates to a gel, obtainable via the methods described herein.

In particular, the gel is a hydrophilic gel and;

$R_2$, $R_3$ and $R_5$ are each independently be selected from C1-C3 linear alkyl, and $R_1$ and $R_4$ are each independently selected from C1-C25 linear alkyl, C3-C25 branched alkyl, C3-C25 cycloalkyl, aryl, heteroaryl, hydrogen, —OH, —CN, halogens, amines, amides, alcohols, ethers, thioethers, sulfones and derivatives thereof, sulfonic acid and derivatives thereof, sulfoxides and derivatives thereof, carbonates, isocyanates, nitrates, acrylates, hydrazine, azines, hydrazides, polyethylenes, polypropylenes, polyesters, polyamides, polyacrylates, and polyurethanes; and when $R_1$ and $R_4$ are alkyl and aryl groups, they may be substituted with one or more substituents selected from CN; OH; azides; esters; ethers; amides; halogen atoms; sulfones; sulfonic derivatives; $NH_2$ or $Nalk_2$, where alk is any $C_1$-$C_8$ straight chain alkyl group, $C_3$-$C_8$ branched or cyclic alkyl group.

Medical Device

One aspect of the invention provides a medical device comprising the gel precursor or hydrophilic gel resulting from the methods of the invention. The term "medical device" should be interpreted in a fairly broad sense. Suitable examples of medical devices (including instruments) are catheters (such as urinary catheters), endoscopes, laryngoscopes, tubes for feeding, tubes for drainage, endotracheal tubes, guide wires, sutures, cannulas, needles, thermometers, condoms, urisheaths, barrier coatings e.g. for gloves, stents and other implants, contact lenses, extra corporeal blood conduits, membranes e.g. for dialysis, blood filters, devices for circulatory assistance, dressings for wound care, and ostomy bags. Most relevant are catheters, endoscopes, laryngoscopes, tubes for feeding, tubes for drainage, guide wires, sutures, and stents and other implants. Particularly interesting medical devices within the context of the present invention are catheters, such as urinary catheters.

The medical device may be coated on at least a surface portion thereof with the gel precursor or hydrophilic gel of the invention. In some embodiments, the hydrophilic gel covers the full (outer) surface of the medical device, and in some other embodiments, only to a part of the surface thereof. In the most relevant embodiments, the hydrophilic gel covers at least a part of the surface (preferably the whole surface) of the medical device that—upon proper use—comes into direct contact with body parts for which the medical device is intended. It may be that the medical device is coated with a cured matrix composition, and the hydrophilic gel is generated upon contact with liquid—either the bodily fluids of the patient, or an activating solution containing water.

EXAMPLE 1

A 50 mL two-neck flask was charged with (4-((bis(2-hydroxyethyl)amino)methyl)phenyl)(phenyl)methanone (0.04 g, 0.13 mmol) and PEG2000 (1.7 g, 0.85 mmol). Moisture was removed from the reaction flask by melting the reactants under vacuum and heating the liquid reaction mixture until all effervescence ceased (approx. 5 min at 80° C.). The flask was allowed to cool under vacuum, fitted with a reflux condenser and flushed with nitrogen. Dry chlorobenzene (10 mL) was added and the reaction mixture was stirred at 60° C. to obtain a homogeneous clear solution. 4,4'-Methylenebis(cyclohexyl-isocyanate) (0.26 g, 0.99 mmol) was added via syringe and the reaction mixture was heated under reflux to 145° C. for 48-60 h. The viscous yellow mixture was cooled to ambient temperature, diluted in toluene (50 mL) and evaporated to dryness. Methanol (125 mL) and water (75 mL) were added to the residue to provide a viscous turbid solution. Evaporation of the mixture gave a gummy solid that was dried in vacuo for 4-6 h at 75° C., leaving a pale yellow solid in nearly quantitative yield (1). $M_w$ 43 kDa, PD=2.4.

EXAMPLE 2

In a procedure similar to the one used in Example 1, a polyurethane was synthesized using (4-(3-(bis(2-hydroxyethyl)amino)propoxy)phenyl)(phenyl)nnethanone (2 wt %), PEG2000 (85 wt %) and 4,4'-methylenebis(cyclohexyl-isocyanate) (13 wt %) as the reactants resulted in a polymer (2) with $M_w$ 43 kDa and PD=2.4 in nearly quantitative yield.

EXAMPLE 3

In a procedure similar to the one used in Example 1, a polyurethane was synthesized using (4-((bis(2-hydroxyethyl)amino)methyl)phenyl)(phenyl)methanone (10 wt %), PEG2000 (72 wt %) and 4,4'-methylenebis(cyclohexyl-isocyanate) (18 wt %) as the reactants resulted in a polymer (3) with $M_w$ 76 kDa and PD=2.12 in nearly quantitative yield.

EXAMPLE 4

In a procedure similar to the one used in Example 1, a polyurethane was synthesized using (4-(3-(bis(2-hydroxyethyl)amino)propoxy)phenyl)(phenyl)methanone (10 wt %), PEG2000 (73 wt %) and 4,4'-methylenebis(cyclohexyl-isocyanate) (17 wt %) as the reactants resulted in a polymer (4) with $M_w$ 78 kDa and PD=2.27 in nearly quantitative yield.

EXAMPLE 5

In a procedure similar to the one used in Example 1, a polyurethane was synthesized using (4-(bis(2-hydroxyethyl)amino)phenyl)(phenyl)methanone (2 wt %), PEG2000 (85 wt %) and 4,4'-methylenebis(cyclohexyl-isocyanate) (13 wt %) as the reactants resulted in a polymer (5) with $M_w$ 37 kDa and PD=1.87 in nearly quantitative yield.

EXAMPLE 6

In a procedure similar to the one used in Example 1, a polyurethane was synthesized using (4-(bis(2-hydroxyethyl)amino)phenyl)(phenyl)methanone (10 wt %), PEG2000 (71 wt %) and 4,4'-methylenebis(cyclohexyl-isocyanate) (19 wt %) as the reactants resulted in a polymer (6) with $M_w$ 34 kDa and PD=1.77 in nearly quantitative yield.

EXAMPLE 7

In a procedure similar to the one used in Example 1, a polyurethane was synthesized using 4-(3-(bis(2-hydroxyethyl)amino)propoxy)-1-chloro-9H-thioxanthen-9-one (2 wt %), PEG2000 (85 wt %) and 4,4'-methylenebis(cyclohexyl-isocyanate) (13 wt %) as the reactants resulted in a polymer (7) with $M_w$ 43 kDa and PD=1.76 in nearly quantitative yield.

EXAMPLE 8

In a procedure similar to the one used in Example 1, a polyurethane was synthesized using 4-(3-(bis(2-hydroxyethyl)amino)propoxy)-1-chloro-9H-thioxanthen-9-one (10 wt %), PEG2000 (74 wt %) and 4,4'-methylenebis(cyclohexyl-isocyanate) (16 wt %) as the reactants resulted in a polymer (8) with $M_w$ 29 kDa and PD=1.62 in nearly quantitative yield.

EXAMPLE 9

In a procedure similar to the one used in Example 1, a polyurethane was synthesized using (4-((bis(2-hydroxyethyl)amino)methyl)phenyl)(phenyl)methanone (2 wt %), Jeffamine D4000 (90 wt %) and 4,4'-methylenebis(cyclohexyl-isocyanate) (8 wt %) as the reactants resulted in a polymer (9) with $M_w$ 42 kDa and PD=1.19 in nearly quantitative yield.

EXAMPLE 10

In a procedure similar to the one used in Example 1, a polyurethane was synthesized using ((4-(3-(bis(2-hydroxyethyl)amino)propoxy)phenyl)(phenyl)nnethanone (2 wt %), Jeffamine D4000 (91 wt %) and 4,4'-methylenebis(cyclohexyl-isocyanate) (7 wt %) as the reactants resulted in a polymer (10) with $M_w$ 49 kDa and PD=1.24 in nearly quantitative yield.

EXAMPLE 11

In a procedure similar to the one used in Example 1, a polyurethane was synthesized using (4-(bis(2-hydroxyethyl)amino)phenyl)(phenyl)methanone (2 wt %), Jeffamine D4000 (90 wt %) and 4,4'-methylenebis(cyclohexyl-isocyanate) (8 wt %) as the reactants resulted in a polymer (11) with $M_w$ 46 kDa and PD=1.23 in nearly quantitative yield.

EXAMPLE 12

In a procedure similar to the one used in Example 1, a polyurethane was synthesized using 4-(3-(bis(2-hydroxyethyl)amino)propoxy)-1-chloro-9H-thioxanthen-9-one (2 wt %), Jeffamine D4000 (91 wt %) and 4,4'-methylenebis(cyclohexyl-isocyanate) (7 wt %) as the reactants resulted in a polymer (12) with $M_w$ 46 kDa and PD=1.24 in nearly quantitative yield.

EXAMPLE 13

An oblate of the pristine polymer from example 1-12 was placed between the two plates in a rheometer (parallel plate configuration, bottom plate is a quartz glass plate) and the distance between the plates was set to 0.3 mm and the temperature to 120° C. The measurements were run with fixed strain of 1% and a constant frequency of 1 Hz. When the loss and storage modules had stabilized, a UV-lamp was turned on, thus irradiating the sample through the bottom plate on the rheometer via a fiber from the lamp. The loss and storage modules were then followed as a function of time, while the UV-lamp was irradiating the sample. Illustrative results of the measurements are shown in FIG. 1. All the samples, except 14, increase their solid content as they are exposed to UV which is seen from the decrease in tan δ. An increase in tan δ signifies an increasing amount of liquid present in the sample. Both samples 11 and 14 appear to degrade when exposed to UV light as both the G' and G" modulus are decreasing, whereas the rest of the samples have increasing modulus when exposed to UV. Likewise values of tan δ below one is obtained for all samples except 11 and 14.

The invention claimed is:
1. A method for the manufacture of a gel, said method comprising the steps of:
  a) providing a matrix composition comprising a polymeric photoinitiator which is the reaction product of:

(4-(3-(bis(2-hydroxyethyl)amino)propoxy)phenyl)(phenyl)methanone, PEG2000, and 4,4'-methylenebis(cyclohexyl-isocyanate);
b) curing the matrix composition obtained in step a) by exposing the matrix composition to UV radiation, and
c) exposing the matrix composition to a swelling medium, thus providing a gel wherein step c) may take place before or after step b).

2. The method according to claim 1, wherein the weight averaged molecular weight of the polymeric photoinitiator is between 29 kDa and 78 kDa.

3. The method according to claim 1, wherein the matrix composition additionally comprises one or more hydrophilic gel-forming polymers and/or hydrophilic gel-forming monomers.

4. The method according to claim 3, wherein the gel-forming polymer is selected from the group consisting of polyacrylates, polyalkylethers, polyurethanes, polyethylene vinyl acetates, polyvinylpyrrolidone and co-polymers and blends thereof.

5. The method according to claim 3, wherein the gel-forming monomer is selected from the group consisting of acrylate monomers, N-vinylpyrrolidone, and epoxide monomers.

6. The method according to claim 1, wherein the matrix composition consists of the polymeric photoinitiator.

7. The method according to claim 1, wherein the swelling medium is selected from the group consisting of water, C1-C5 alcohols, glycerol and polyethylene glycol (PEG).

8. The method according to claim 1, wherein the swelling medium comprises water, and the gel thus produced is a hydrogel.

9. The method according to claim 1, wherein step c) takes place before step b).

10. The method according to claim 1, consisting of steps a), b) and c).

* * * * *